US00PP30403P2

(12) United States Plant Patent
Egger

(10) Patent No.: US PP30,403 P2
(45) Date of Patent: Apr. 16, 2019

(54) ***AGASTACHE* PLANT NAMED 'TNAGAPBY'**

(50) Latin Name: ***Agastache* hybrid**
Varietal Denomination: TNAGAPBY

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,025

(22) Filed: Jan. 25, 2018

(51) Int. Cl.
*A01H 5/02* (2018.01)

(52) U.S. Cl.
USPC ..... Plt./399

(58) Field of Classification Search
USPC ..... Plt./399
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Agastache* plant is provided, characterized by butter yellow flowers in good size inflorescences, a long bloom time, a very short, compact, bushy habit, good cold tolerance, and excellent vigor.

1 Drawing Sheet

Botanical denomination: *Agastache* hybrid.
Variety designation: 'TNAGAPBY'.

BACKGROUND OF THE INVENTION

The present invention relates to a new and distinct cultivar of *Agastache*, given the name, 'TNAGAPBY'. *Agastache* is in the family Lamiaceae. This new cultivar is one of several selections of new *Agastache* using hardy and dwarf *Agastache* species in the breeding lines to provide hardiness and compactness. The new cultivar is a selection from the cross between the proprietary seedlings *Agastache* '224-1', as the seed parent, and *Agastache* '227-3', as the pollen parent. Both are proprietary, unpatented seedlings. The new cultivar was selected for its very compact habit, its hardiness, and its good size inflorescences of butter yellow flowers.

The trademark designation for the claimed plant is 'Poquito™ Butter Yellow'.

Compared to the seed parent, *Agastache* '224-1', the new cultivar is shorter with larger inflorescences.

Compared to the pollen parent, *Agastache* '227-3', the new cultivar is better branched and shorter.

Compared *Agastache* 'Kudos Yellow' (U.S. Plant Pat. No. 26,563), the new cultivar is more compact and shorter.

This plant exhibits the following characteristics that make it unique:

1. butter yellow flowers in good size inflorescences,
2. a long bloom time,
3. a very short, compact, bushy habit,
4. good cold tolerance, and
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old plant of the new cultivar grown in a garden in full sun in Canby, Oreg.

FIG. 2 shows a nine-month-old *Agastache* 'TNAGAPBY' growing in the trial field in mid-July in Canby, Oreg.

DETAILED PLANT DESCRIPTION

The following is a detailed description of the new *Agastache* cultivar based on observations of 18-month-old specimens in mid-July growing in full sun in a garden in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form*.—Upright, bushy.
*Type*.—Herbaceous perennial.
*Cold hardiness*.—USDA Zone 6-10.
*Size*.—Grows to 40 cm wide and 42 cm tall to the top of the flowers.
*Vigor*.—Excellent.
*Branching*.—About 20 main stems from the base, these branch at every node.
*Stem*.—Square in cross section, grows to 5 mm wide and 23 cm tall to the first flower, pubescent, Yellow Green 146A, internodes range from 1 cm to 4 cm long.
*Roots*.—White 155B, fibrous, plants root easily from stem tip cuttings.

Leaf:

*Type*.—Simple.
*Arrangement*.—Opposite.

*Shape*.—Ovate.
*Venation*.—Pinnate.
*Margins*.—Coarsely serrate to entire.
*Apex*.—Acute.
*Base*.—Cuneate.
*Blade size*.—Grows to 35 mm long and 22 mm wide.
*Surface texture*.—Pubescent on both sides.
*Petiole description*.—Grows to 11 mm long and 2 mm wide, pubescent, Yellow Green 147B.
*Leaf color*.—Top side Green N137B with vein Yellow Green 147C, bottom side closest to Yellow Green 147B with vein 147C.
*Fragrance*.—Aromatic.

Inflorescence:
*Type*.—Terminal spike with up to 11 congested whorls.
*Number of flowers*.—Up to 350 per spike.
*Size of inflorescence*.—Grows to 13 cm tall and 4 cm wide.
*Peduncle*.—Grows to 4 cm tall and 2.5 mm wide, pubescent, Yellow Green 146C.
*Pedicel*.—Grows to 2.5 mm long, pubescent, Yellow Green 146C.
*Bloom period*.—June through frost in Canby, Oreg. (with better repeat bloom if plants are cut back).

Flower Bud:
*Size*.—9 mm long and 4 mm wide at the widest point prior to opening.
*Description*.—Tubular.
*Surface texture*.—Pubescent.
*Color*.—Yellow Orange 16C on tube blending to Orange 26A on tip.

Flower:
*Type*.—Zygomorphic.
*Shape*.—Bilabiate, tubular.
*Size*.—29 mm long and 7 mm wide.
*Corolla description*.—27 mm long and spreads to 7 mm wide; outside and inside Yellow Orange 18A with Orange 26C tint on upper 4 lobes, glabrous inside and pubescent outside, tube 20 mm long and 1 mm to 5 mm wide; 2 upper lobes joined, each 4 mm long and 3.5 mm wide, each oblong, tips acute, margins entire; three lower lobes, two spreading sideways and curl back, each 3 mm long and 2.5 mm wide, tip acute, margin entire; bottom lobe, reflexed and cupped at the bottom, broadly obovate, notched at the tip, margin irregularly crenulate, 4 mm wide and 4 mm deep.
*Calyx description*.—Campanulate, 8 mm long and 2.5 mm wide, pubescent outside and glabrous inside, 5 lobed, lobes lanceolate, 2 mm long and 1 mm wide, entire, acute, Yellow Green 146C.
*Pistil description*.—29 mm long, ovary 1 mm long and 1 mm wide, Yellow Green 147C, style 27 mm long, White NN155A, stigma two-to thee-parted, 1 mm deep, White NN155A.
*Stamen description*.—4 in number, paired and exerted, top two 17 mm long and bottom two 15 mm long, filaments Yellow Orange 19B, anthers 0.5 mm long, Orange 29C , pollen Orange 27D.
*Fragrance*.—Aromatic.
*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

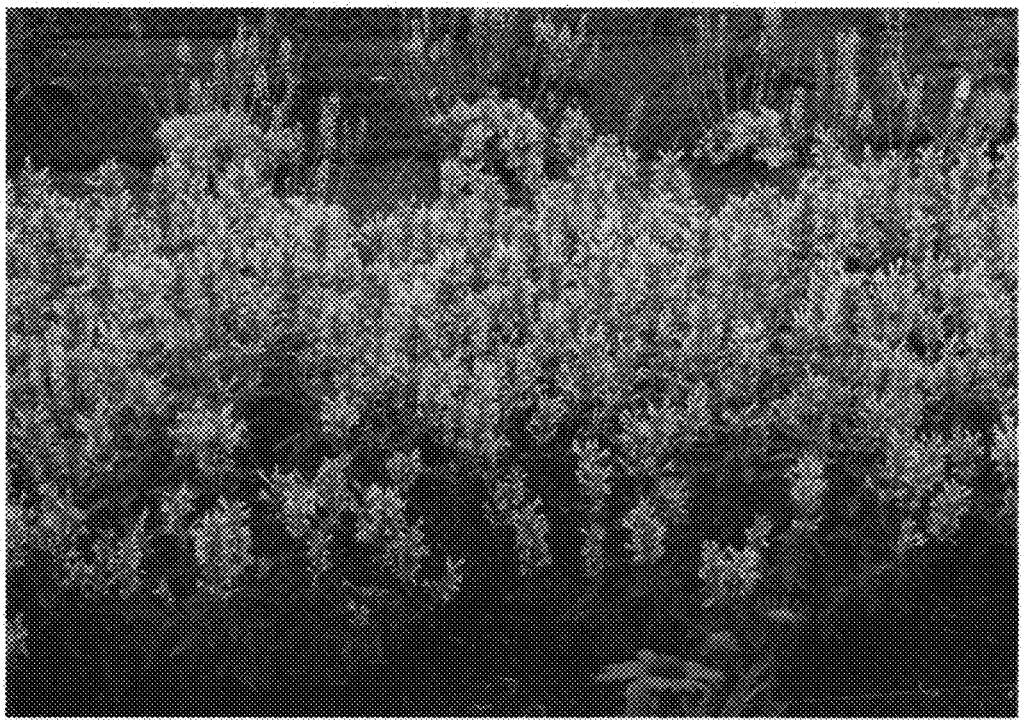

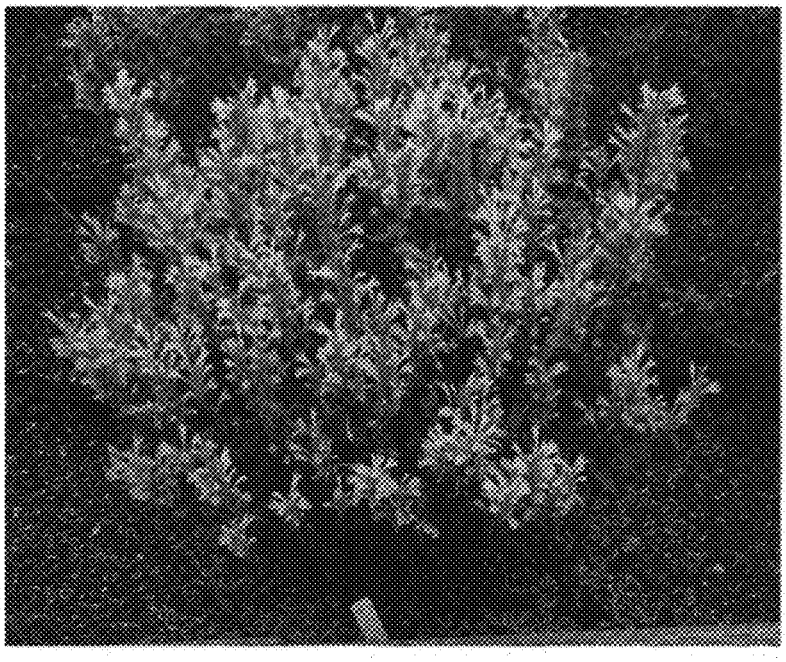
FIG. 1 on left,
FIG. 2 below